United States Patent
Pulliam et al.

(10) Patent No.: US 6,426,796 B1
(45) Date of Patent: Jul. 30, 2002

(54) FIBER OPTIC WALL SHEAR STRESS SENSOR

(75) Inventors: Wade J. Pulliam; Joseph A. Schetz; Mark E. Jones, all of Blacksburg; Kent A. Murphy, Troutville, all of VA (US)

(73) Assignees: Luna Innovations, Inc.; VA Tech Intellectual Properties, Inc., both of Blacksburg, VA (US)

(*) Notice: Subject to any disclaimer, the term of this patent is extended or adjusted under 35 U.S.C. 154(b) by 0 days.

(21) Appl. No.: 09/406,665

(22) Filed: Sep. 27, 1999

Related U.S. Application Data

(60) Provisional application No. 60/102,079, filed on Sep. 28, 1998.

(51) Int. Cl.[7] ................................................ G01B 9/02
(52) U.S. Cl. ........................ 356/501; 356/477; 356/505
(58) Field of Search ................................. 356/477, 478, 356/480, 482, 498, 501, 35.5, 506, 505, 507

(56) References Cited

U.S. PATENT DOCUMENTS

| | | | |
|---|---|---|---|
| 4,806,012 A | | 2/1989 | Meltz et al. |
| 5,052,228 A | * | 10/1991 | Haritonidis .................. 73/705 |
| 5,301,001 A | | 4/1994 | Murphy et al. |

OTHER PUBLICATIONS

W.Pulliam, M. Jones, J.A. Schetz, K. Murphy, "Fiber Optic Pressure/Skin Friction Gage for Supersonic Flow Applications," International Congress on Instrumentation in Aerospace Simulation Facilities, Pacific Grove, CA, Sep. 27–Oct. 2, 1997.

A. Padmanabhan, H.D. Goldberg, M.A. Schmidt, K.S. Breuer, "A Silicon Micromachined Sensor for Shear Stress Measurements in Aerodynamic Flows," AIAA 96–0422, Jan. 15–18, 1996, pp. 1–9.

V. Tarasov, S. Fonov, A. Morozov, "New Gauges for Direct Skin Friction Measurements,"paper handed–out at International Congress on Instrumentation in Aerospace Simulation Facilities, Pacific Grove, CA, Sep. 27–Oct. 2, 1997, pp. 1–7.

M. Meheregany, R.G. Deanna, E. Reshotko, "Microelectromechanical Systems for Aerodynamics Applications," AIAA96–0421, Jan. 15–18, 1996, pp. 2–12.

M. Acharya, J. Bornstein, M.P. Escudier, V. Vokurka, "Development of a Floating Element for the Measurement of Surface Shear Stress," AIAA Journal, Mar. 1985, vol. 23, No. 1, pp. 410–415.

J.A. Schetz, "Direct Measurement of Skin Friction in Complex Fluid Flows," Applied Mechanical Review, Nov. 1997, vol. 50, part 2, pp. S198–S203.

K.C. Winter, "An Outline of the Techniques Available for the Measurement of Skin Friction in Turbulent Boundary Layers," Prog. Aerospace Sci., 1977, vol. 18, pp. 1–57.

J.A. Schez, B. Nerney, "Turbulent Boundary Layer with Injection and Surface Roughness," AIAA Journal, Sep. 1977, vol. 15, No. 9, pp. 1288–1294.

* cited by examiner

*Primary Examiner*—Frank G. Front
*Assistant Examiner*—Andrew H. Lee
(74) *Attorney, Agent, or Firm*—Joy L. Bryant

(57) ABSTRACT

A fiber optic wall shear stress sensor is presented. The sensor comprises a floating head supported by a physical arrangement. At least one optical fiber is positioned in an operable relationship to the floating head wherein an interferometric region is formed between the floating head and each optical fiber. The interferometric region changes in response to a shear force on the floating head.

37 Claims, 10 Drawing Sheets

FIBER OPTIC WALL SHEAR STRESS SENSOR

CROSS-REFERENCE TO RELATED APPLICATIONS

This application claims the benefit of U.S. Provisional Application No. 60/102,079, entitled "Fiber Optic Wall Shear Stress Sensor," filed Sep. 28, 1998, hereby incorporated by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of contract no. F33615-97-C-2713 awarded by Air Force Research Labs (Wright Patterson Air Force Base).

FIELD OF THE INVENTION

The present invention relates to wall shear stress sensors. In particular, it relates to a fiber optic wall shear stress sensor.

BACKGROUND OF THE INVENTION

A significant fraction of the total resistance to motion on airplanes and ships is due to surface friction, or skin friction. Measuring and determining this friction is complex and further complicated by the limited availability of skin friction gages. This is in contrast to the availability of gages for pressure, temperature and strain. Early work in this area involved obtaining data in pipe flows, where the wall shear can be directly related to the pressure drop, which is relatively simple to measure accurately. By measuring the small frictional force exerted on a movable element of the surface, one is able to obtain direct measurements of wall shear stress. These types of measurements work well for laminar, transitional and turbulent flows without prior knowledge of the state of the flow.

A great number of techniques for the measurement of wall shear stress have been devised over the years, ranging from inferring the skin friction from measuring the boundary layer profile or using some correlation or analogy to the direct measurement of the force on a surface. Although all of these techniques can be shown to work for some flow regime, indirect methods, such as Stanton tubes, Preston tubes, and surface hot-wire techniques to name a few, have not been shown to be reliable for complex flows such as 3D and/or unsteady cases with rough wall, curved walls, flows with injection or suction, or high-speed flows, especially those with high enthalpies, combustion and/or impinging shocks. Alternatively, direct measurements do not require any foreknowledge of the flow or its properties and can provide accurate results all the regimes mentioned above.

Direct measurements, refers to techniques that separate a small element, referred to as a floating head, from the wall and measures the tangential force that the flow imparts on it. Direct measurements are the most believable of all the techniques. The sensor is measuring the actual shear on the surface, without respect to the fluid, the state of the boundary layer, or chemical reactions. Since the floating head is level with the wall, the measurement is non-intrusive to the flow. The forces are very small, sometimes requiring large floating heads and expensive instrumentation to obtain accurate results. The direct measurement technique generally falls into two categories, nulling and non-nulling.

In the nulling design, called this because the floating head is returned to its null (or original) position, the floating head is acted upon by shear, but the sensor provides a restoring force to the head to keep it in place. The magnitude of that restoring force is monitored, which is equal to the shear force acting on the floating head. In one example, the floating head was supported by a beam which pivoted around a spring near the base. The movement of the head was sensed by a pair of capacitance plates, with an electromagnet used to supply the restoring force. Other nulling designs have required mechanical linkages and motors to return the head to the null position. Although the nulling design does remove some of the possible error introduced by the movement of the head, the sensors are very complex, mechanically unreliable, and have a slow time response, on the order of seconds.

In a non-nulling design, the floating head is allowed to deflect under the shearing load. This type of design is much simpler than a nulling design, allowing the removal of the restoring force mechanism and thus making much smaller time responses possible. However, this arrangement does allow the structure of the sensor to flex and this variation may introduce spurious results.

Another type of non-nulling gage is a design where the floating head is supported by tethers around its periphery. This design is sensitive to normal pressure changes because the tethers are more sensitive to motion normal to the wall than parallel to it. In macro-designs of the tether sensor, where the displacement was measured by strain gages mounted on the tethers, the sensor was not only sensitive to normal pressures, but also to temperature changes as the strain gages were very near the flow. In supersonic flows, wall temperature can change significantly during a test. However, the heat flux boundary conditions are significantly different at the floating head than the rest of the wall, leading to significant temperature differences and, therefore, significant errors in the shear measurement. In micromachined designs, the strain gages have been replaced by capacitance or by an external laser/photoiode system. However, the drawbacks of the table-top design remain, limiting the use of the sensor to simple flows without large temperature or pressure variation.

Another non-nulling design is a cantilever beam concept. In this design, the floating head is attached to a single cantilever beam which flexes with the application of shear to the head. The displacement is measured by the strain caused by the displacement at the base of the beam. If the displacements are kept to a minimum, the issue of head protrusion into the flow is negligible. This design offers high stiffness for normal forces, while being relatively weak for tangential forces, providing a sensor that is insensitive to normal pressure variations. The concept is very simple, rugged and has a small time response. If the sensing head is prepared from similar materials as the surrounding wall, errors from temperature mismatches will be minimized. Also, the concept can be easily extended to measure in two directions, removing the directional ambiguity of other designs.

Winter ("An Outline of the Techniques Available for the Measurement of Skin Friction in Turbulent Boundary Layers," *Prog. Aerospace Sci.*, 1977, Vol. 18, pp. 1–57) was able to use resistance strain gages in a large balance, which allowed sensitive measurements in a static environment. Schetz and Nerney ("Turbulent Boundary Layer with Injection and Surface Roughness," *AIAA Journal*, 1977, Vol. 15, No. 9, pp. 1288–1294) made the next step to semi-conductor strain gages, improving the output 100 fold. A series of skin friction sensors based on strain gages mounted on the cantilever beam in a non-nulling arrangement have also been produced that are useful for measuring subsonic or cool supersonic flows. However, as the Mach number range increases, hot flows are encountered. In addition, the study of supersonic flows with injection of combustible gases such as hydrogen also necessitated a new design of skin friction gages. High enthalpy flows are simulated using an object. During this simulation, the skin friction gage encounters both high temperatures and high electromagnetic field environments.

Acharya et al. ("Development of a Floating Element for the Measurement of Surface Shear Stress," *AIAA Journal*, March 1985, Vol. 23, No. 1, pp. 410–415) describe a floating-element instrument having a central component which is a tension galvanometer which supports the element itself. The position of a target on the back of the element is determined using a fiber-optic scanner. A reflector is lined-up perfectly with the fiber. The reflector is only partially reflective, and therefore, only part of the light is returned through the fiber. The returning light is shined on a photodiode and transformed to voltage. The nulling part of the circuit moves the head and the reflector back to the same voltage, which is the same location on the reflector. This design is extremely complicated requiring a feedback mechanism and an actuator to rezero the head. The alignment of the fiber and the reflector must be precise, making construction of the device difficult. Use of the partial reflection reflector limits the temperature that the sensor can be used. Since all of the electronics are internal, the sensor is large, complex and temperature sensitive. Moreover, this design can only be used for nulling applications.

By the present invention, the sensing technology has moved to an interferometric use of fiber optics, allowing a design principle based on deflection instead of strain. It has been discovered that an interferometric use of fiber optics not only offer increased sensitivity to displacement but also new design concepts that increase sensitivity to shear. This permits the area of the floating head and the length of the cantilever beam to be decreased and, therefore, the whole sensor package may be miniaturized.

Fiber optic sensors provide a means for overcoming the temperature and electromagnetic field sensitivity issues. In particular, optical fiber sensors: 1) have an inherent immunity to electromagnetic interference; 2) are capable of avoiding ground loops; 3) are capable of responding to a wide variety of measurands; 4) have excellent resolution; 5) are capable of avoiding sparks; and 6) can operate at temperatures ranging from 800° C. to 1900° C. Murphy et al. (U.S. Pat. No. 5,301,001) describe a fiber optic strain sensor based on the extrinsic Fabry-Perot interferometer (EFPI). This sensor is a displacement sensor wherein a single mode silica fiber transmits light from a laser diode to the sensor element. The sensor comprises a single mode fiber, used as an input/output fiber, and a multimode fiber, used purely as a reflector, to form an air gap within a silica tube that acts as a Fizeau cavity. The single mode fiber transmits light from a laser diode to the sensor element. At the opposite end of the input fiber, the laser light signal is partially reflected and partially transmitted across the gap separating the ends of the input fiber and the multimode fiber. The reference signal and the reflected signal interfere and propagate back through the input fiber to a photodiode detector. Changes in the separation distance between the surfaces of the fibers produce a modulation of the output signal current. The strain sensor is used to measure small displacements by attaching the sensor to the surface of the material to be measured. As the strain of the material is transferred to the sensor, the separation distance between the surfaces of the fibers changes and the resulting displacement is measured. The strain is inferred from the resulting displacement. Although previous wall shear stress sensors had a strain measurement to infer the shear stress, the EFPI sensor as configured for strain measurements proved to be ineffective for the stated purpose. Wall shear stress measurements necessarily take place in fluid flows which have static pressure different than that of the atmosphere at sea level. The EFPI as configured for strain measurements is slightly pressure sensitive, but when compared to the magnitude of the strain in a conventionally-configured wall shear stress sensor caused in a normal fluid flow, this sensitivity is large and ruins the measurement. Applicants discovered that it was no longer necessary to rely on a strain measurement, and that the wall shear stress sensor should be configured completely around a displacement measurement. This removed the pressure sensitivity and increased the overall sensitivity of the sensor.

An object of the present invention is to provide a fiber optic wall shear stress sensor based on deflection type measurements.

Another object of the present invention is to provide a fiber optic wall shear stress sensor that is capable of deflecting due to a shear force.

Another object of the present invention is to provide a fiber optic wall shear stress sensor that is less sensitive to temperature changes than previous sensor designs.

SUMMARY OF THE INVENTION

These and other objects of the invention were achieved by the present invention which is a fiber optic wall shear stress sensor. The sensor comprises a floating head supported by a physical arrangement and at least one optical fiber positioned in an operable relationship to the floating head. An interferometric region is formed between the floating head and each optical fiber. The interferometric region changes in response to a shear force on the floating head.

In another embodiment of the invention, the fiber optic wall shear stress sensor comprised a floating head supported by a physical arrangement. A reflector is positioned in an operable relationship to the floating head such that the reflector moves in response to the floating head. At least one optical fiber is positioned in an operable relationship to the reflector. An interferometric region is formed between each optical fiber and the reflector. The interferometric region changes in response to a shear force on the floating head.

When measuring wall shear stress with the fiber optic sensor of the present invention, the sensor is provided. Light is directed through the optical fiber. The fiber optic wall shear stress sensor is exposed to a fluid flow such that the floating head is deflected. This deflection causes a change in the interferometric region and light is reflected back through the optical fiber. If the arrangement with the reflector is being used, the light is reflected from the reflector back through the optical fiber. The change in the interferometric region is measured and correlated to the a wall shear stress.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE PREFERRED EMBODIMENTS

Figure 1:
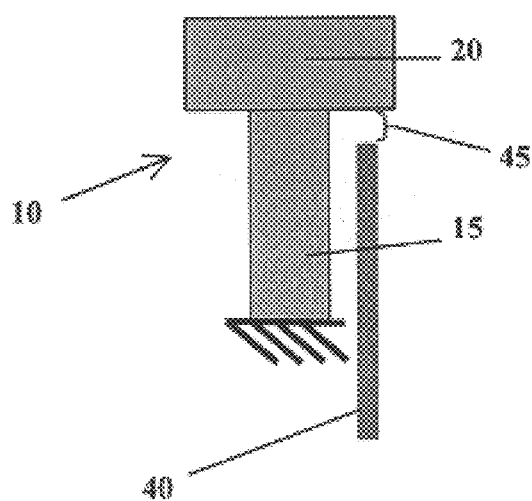
FIG. 1 is a side view of the fiber optic wall shear stress sensor of the present invention where the interferometric region is formed between a surface of the floating head and an optical fiber.

Referring now to the Figures where similar elements are numbered the same, FIG. 1 depicts a side view of the fiber optic wall shear stress sensor 10 of the present invention. The sensor 10 comprises a floating head 20 supported by a physical arrangment 15. For the purpose of this specification and the appended claims, a floating head is defined as a device having a gap surrounding it such that the device is allowed to move freely. The floating head 20 is either moveable and non-nulling or is nulling. Preferably, the floating head 20 is moveable and non-nulling. The physical arrangement 15 which supports the floating head 20 is any physical arrangement known to those skilled in the art and may be as simplistic as a properly prepared surface. More specifically, the physical arrangement 15 is selected from the group consisting of: a cantilever beam, a spring, a flexure, and an elastic support. Preferably, the physical arrangement 15 is a cantilever beam. At least one optical fiber 40 is positioned in an operable relationship to the floating head 20 wherein an interferometric region 45 is formed between the floating head 20 and each optical fiber 40. The interferometric region 45 is the gap or distance between the surface of the floating head 20 and the tip of the optical fiber 40. The interferometric region 45 changes in response to a shear force on the floating head 20. The optical fiber 40 may have a smooth or straight end or may have an angled polished end. The optical fiber 40 serves as both an input fiber and an output fiber. However, separate optical fibers may be used for an input fiber and output fiber as well. Although the invention works well using one optical fiber 40 using a pair of optical fibers affords certain advantages. In particular, using a pair of optical fibers allows for the subtraction of errors which result from changes in temperature. For example, as the physical arrangement undergoes changes in temperature and expands, it bends changing the interferometric region (gap) between the fiber and the floating head. Thus the size of the interferometric region (gap) between the optical fiber and the floating head may be large on one side of the physical arrangement and small on the other side. As the temperature increases, the size of the interferometric region (gap) on both sides of the floating head gets larger. Having two measurements allows for temperature changes to be subtracted out.

Figure 2:
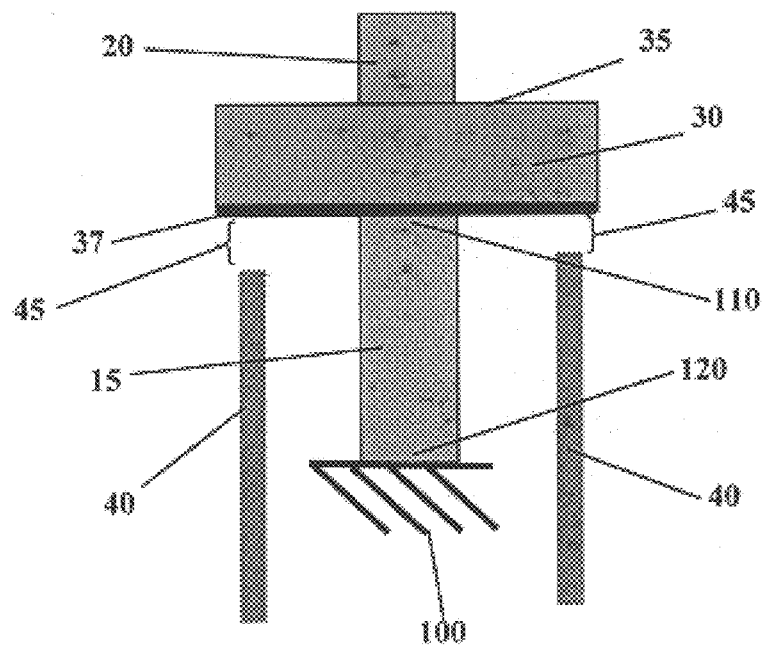
FIG. 2 is a side view of the fiber optic wall shear stress sensor of the present invention where a reflector is positioned in an operable relationship to the floating head and where the interferometric region is formed between the reflector and at least one optical fiber.

FIG. 2 depicts an alternative embodiment of the invention where the floating head 20 is supported by a physical arrangement 15 such as a cantilever beam; a spring; a flexure; or an elastic support. Preferably, the physical arrangement is a cantilever beam. The floating head is either moveable and non-nulling or nulling. A reflector 30 is positioned in an operable relationship to the floating head such that it moves in response to the floating head. The reflector 30 may be any reflector known to those skilled in the art and in particular is either a portion of the physical arrangement 15 or a surface of the floating head 20. The reflector 30 shown in FIG. 2 is larger than the floating head 20 which is attached to an upperside 35 of the reflector 30. The cantilever beam 15 has a first end 110 that is attached to a portion of an underside 37 of the reflector 30. A second end 120 of the cantilever beam 15 is supported by a support 100. At least one (preferably, two) optical fiber 40 is positioned in an operable relationship to the reflector 30 and as shown in the figure, the underside 37 of the reflector 30, to receive a reflection therefrom; allow for measurements to be made in two directions; and to compensate for temperature changes. When the optical fiber 40 is straight ended, it is positioned parallel to the cantilever beam 15. However, if the optical fiber 40 has an angled polished end, it is positioned perpendicular to the cantilever beam 15. This relationship is such that an interferometric region 45 is formed between each optical fiber 40 and the underside 37 of the reflector 30. The interferometric region 45 changes in response to a shear force on the floating head 20.

Figure 3A:
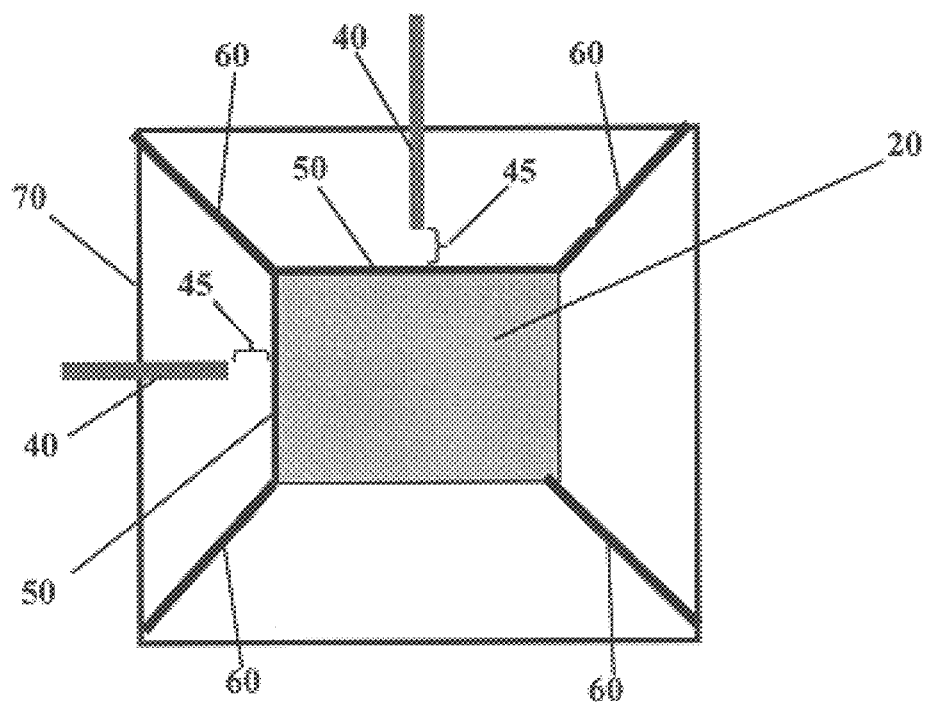
FIG. 3A is a top view of a physical arrangement of the fiber optic wall shear stress sensor of the present invention where the floating head is attached to a support by tethers and where the interferometric region is formed between a surface of the floating head and at least one optical fiber.
Figure 3B:
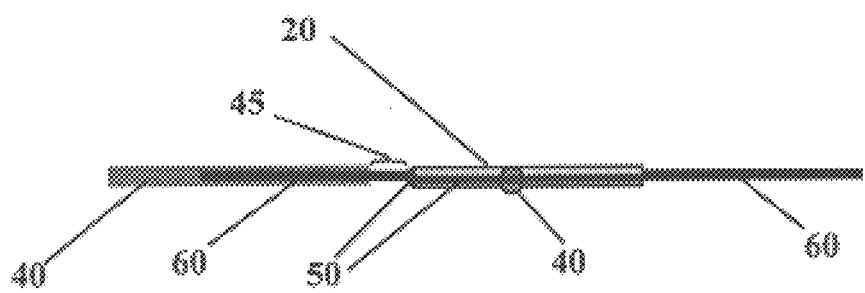
FIG. 3B is a side view of a physical arrangement of the fiber optic wall shear stress sensor of the present invention where the floating head is attached to a support by tethers and where the interferometric region is formed between a surface of the floating head and at least one optical fiber.

The sensor of the present invention may be configured in any number of ways depending on the test parameters and the desired results. FIGS. 3A and 3B depict one physical arrangement wherein the floating head 20 is supported by a plurality of tethers 60 attached to a support structure 70. The support structure 70 may be a housing. A tether is defined as a thin beam and may be approximately 10 microns wide and 30 microns deep. At least one, preferably two, optical fibers 40 are positioned in relationship to the floating head 20 such that an interferometric region 45 is formed between each optical fiber 40 and a surface 50 of the floating head 20. Each optical fiber 40 has either a straight end or an angled polished end. Having two optical fibers 40 present in the arrangement allows measurements to be taken in two directions.

Figure 4A:
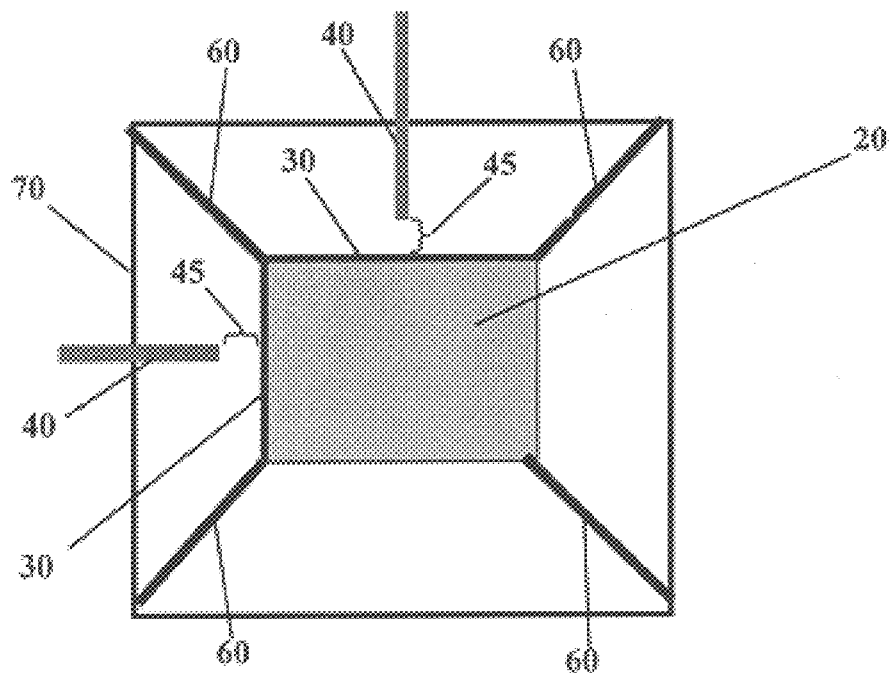
FIG. 4A is a top view of a physical arrangement of the fiber optic wall shear stress sensor of the present invention where the floating head is attached to a support by tethers and where the interferometric region is formed between a reflector and at least one optical fiber.
Figure 4B:
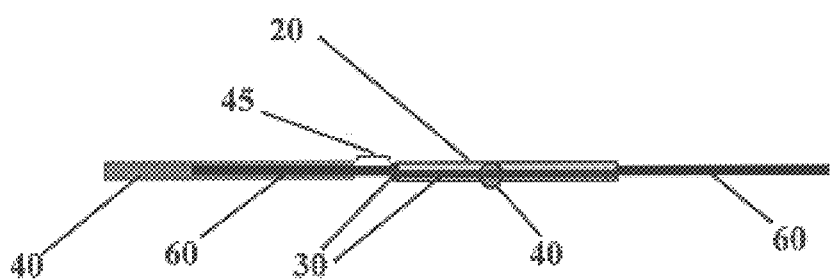
FIG. 4B is a side view of a physical arrangement of the fiber optic wall shear stress sensor of the present invention where the floating head is attached to a support by tethers and where the interferometric region is formed between a reflector and at least one optical fiber.

FIGS. 4A and 4B show a similar physical arrangement for an alternative embodiment where a reflector 30 is attached to the floating head 20. The floating head 20 is supported by a plurality of tethers 60 that are attached at one end to a support structure 70, such as a housing, and at the other end to the floating head 20. The separate reflector 30 is of any configuration known to those skilled in the art. At least one optical fiber (preferably two as shown) 40 is positioned in relationship to the reflector 30 to receive a reflection therefrom. Employing two optical fibers 40 allows for measurement in two directions. Each optical fiber has either a straight end or an angled polished end. The interferometric region 45 is formed between each optical fiber 40 and the reflector 30.

Figure 5:
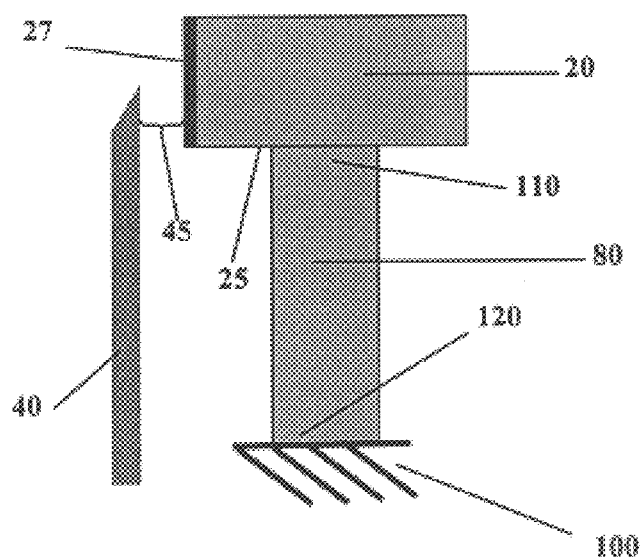
FIG. 5 is a cross-sectional view of a physical arrangement of the fiber optic wall shear stress sensor of the present invention where the floating head is supported on a catilever beam and the interferometric region is formed between a side of the floating head and the optical fiber.

FIG. 5 shows another arrangement where the floating head 20 has a side 27 serving as a reflector and an underside 25. The floating head 20 is supported on a portion of the underside 25 by a first end 110 of at least one cantilever beam 80. A second end 120 of the cantilever beam 80 is supported by a support 100. An interferometric region 45 is formed between each optical fiber 40 and the side 27 of the floating head 20 serving as a reflector. In the figure, the optical fiber 40 is shown having an angled polished end such that the interferometric region 45, is formed between the angled polished end of the optical fiber 40 and the side 27 of the floating head serving as the reflector.

Figure 6:
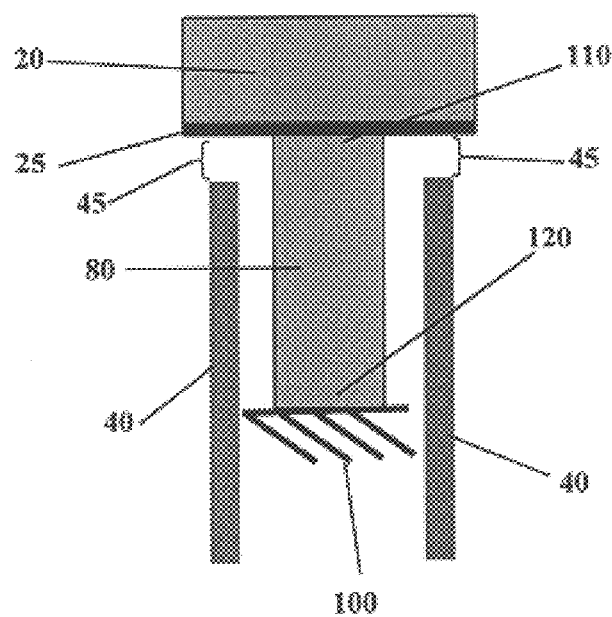
FIG. 6 is a cross-sectional view of a physical arrangement of the fiber optic wall shear stress sensor of the present invention where the floating head is supported on a catilever beam and the interferometric region is formed between the underside of the floating head and the optical fiber.

FIG. 6 depicts an arrangement where the floating head 20 having an underside 25 serving as a reflector is supported on the underside by a first end 110 of at least one cantilever beam 80. The second end 120 of the cantilever beam 80 is supported by a support 100. A least one optical fiber 40, preferably four optical fibers, are positioned perpendicular to the underside 25 of the floating head 20. An interferometric region 45 is formed between each optical fiber 40 and the underside 25 of the floating head 20 serving as a reflector. By using four optical fibers at distinct quadrants, measurements may be made in two directions and temperature changes may be compensated for. Each optical fiber 40 has either a straight end or an angled polished end.

Figure 7A:
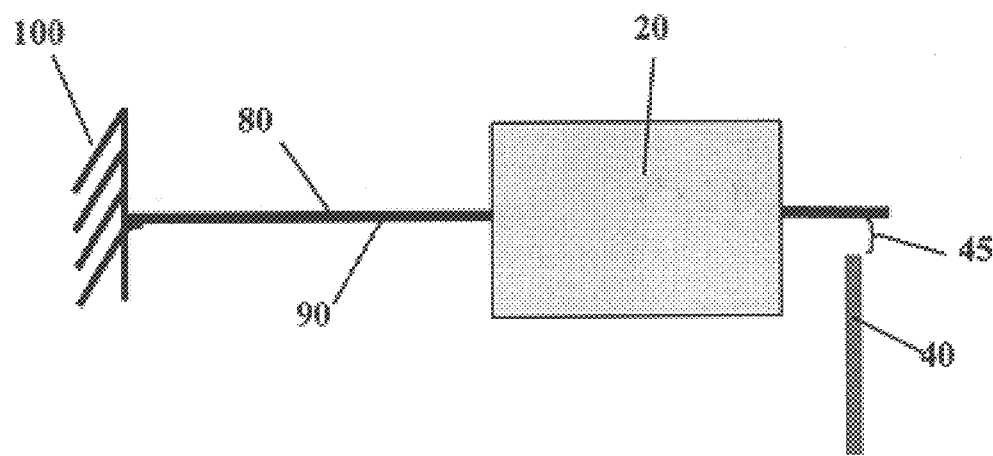
FIG. 7A is a top view of a physical arrangement of the fiber optic wall shear stress sensor of the present invention where the floating head is supported on a catilever beam and the interferometric region is formed between a side of the cantilever beam and the optical fiber.
Figure 7B:
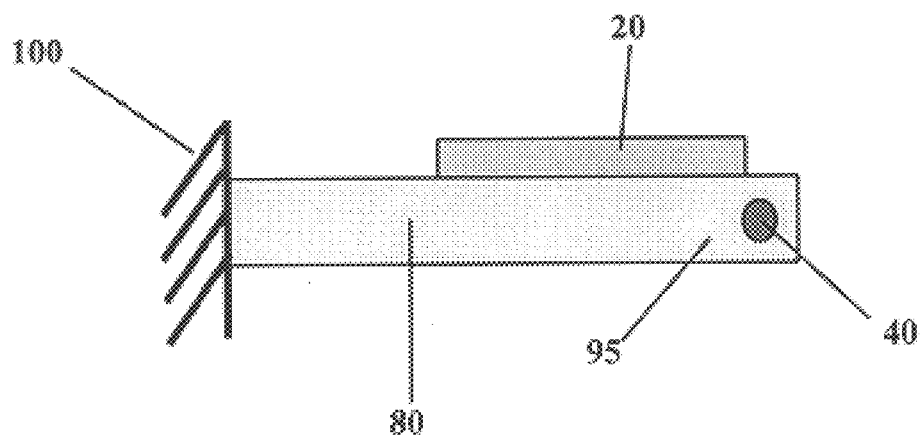
FIG. 7B is a side view of a physical arrangement of the fiber optic wall shear stress sensor of the present invention where the floating head is supported on a cantilever beam and the interferometric region is formed between a side of the cantilever beam and the optical fiber.

FIGS. 7A and 7B show a low profile design for the physical arrangement. In this design, at least one cantilever beam 80 supports the floating head 20 and serves as the reflector. The figure shows the simplest configuration where there is only one cantilever beam 80 supporting the floating head 20. The cantilever beam 80 rests on a support 100 and has a first side 90 and a second side 95. The floating head 20 is supported on the first side 90 of the cantilever beam 80. At least one optical fiber 40 is positioned in relationship to the second side 95 of the cantilever beam 80 such that an interferometric region 45 is formed therebetween. In an alternative embodiment (not shown), the optical fiber has an angled polished end, and the angled polished end is positioned to receive a reflection from the second side of the cantilever beam. In these types of arrangements, the cantilever beam bends when exposed to a wall shear stress. In turn, there is a deflection (both rotational and translational) at the location of the optical fiber, which is correlated back to the wall shear stress. This type of arrangement only permits measurements to be taken from one direction.

Figure 8A:
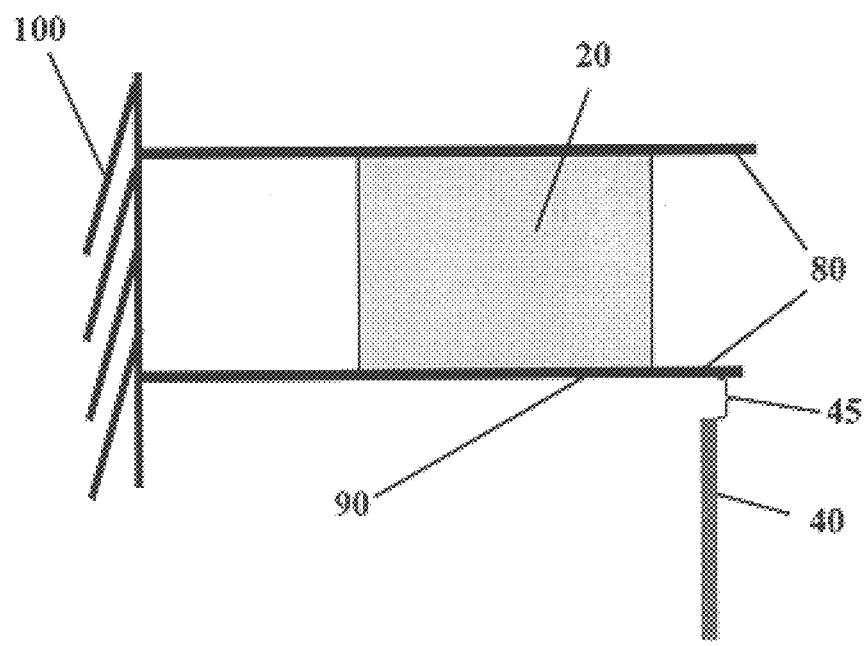
FIG. 8A is a top view of a physical arrangement of the fiber optic wall shear stress sensor of the present invention where the floating head is supported on a pair of cantilever beams and the interferometric region is formed between a side of one of the cantilever beams and the optical fiber.
Figure 8B:
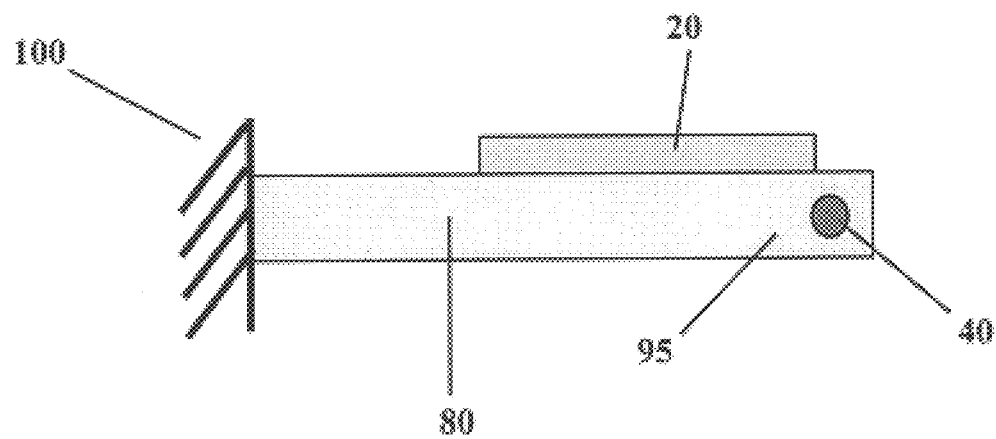
FIG. 8B is a side view of a physical arrangement of the fiber optic wall shear stress sensor of the present invention where the floating head is supported on a pair of cantilever beams and the interferometric region is formed between a side of one of the cantilever beams and the optical fiber.

FIGS. 8A and 8B shows a flexure arrangement, where the floating head 20 is attached to a pair of cantilever beams 80 which are positioned on a support 100. In this arrangement, each cantilever beam 80 has a first side 90 and a second side 95. The floating head 20 is supported on the first side 90 of each cantilever beam. The pair of cantilever beams 80 serves to restrict the rotational motion of the floating head 20. An optical fiber 40 having a straight end or an angled polished end, is positioned with respect to the second side 95 of one of the cantilever beams 80 serving as a reflector. The interferometric region 45 is formed therebetween. This type of arrangement only permits measurements to be taken from one direction.

Figure 9A:
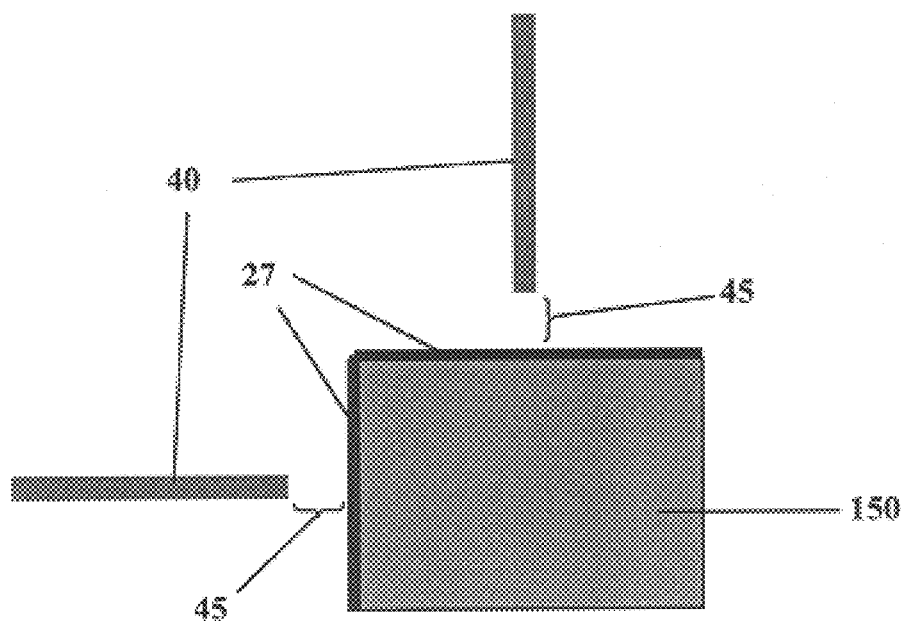
FIG. 9A is a bottom view of a physical arrangement of the fiber optic wall shear stress sensor of the present invention where the floating head is supported on an elastic base and the interferometric region is formed between a side of the floating head and the optical fiber.
Figure 9B:
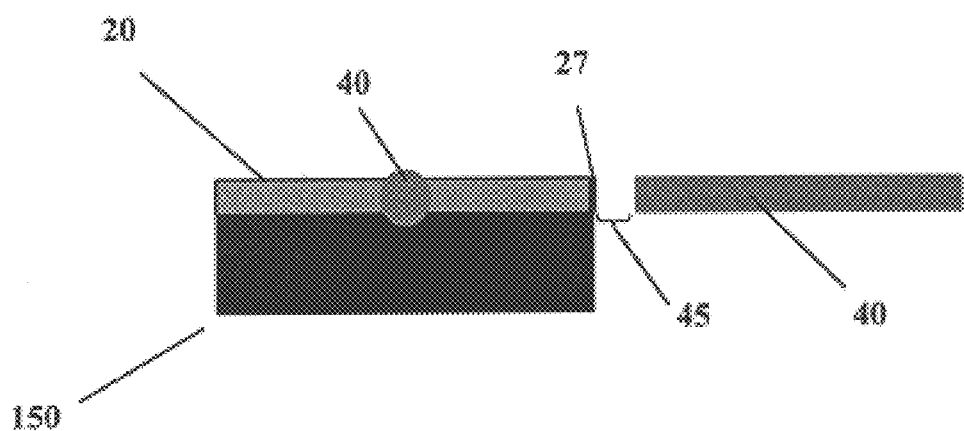
FIG. 9B is a side view of a physical arrangement of the fiber optic wall shear stress sensor of the present invention where the floating head is supported on an elastic base and the interferometric region is formed between a side of the floating head and the optical fiber.

FIGS. 9A and 9B show an arrangement where the underside of the floating head 20 is attached to an elastic base 150. A side 27 of the floating head 20 serves as a reflector. An optical fiber 40 is positioned with respect to the side 27 of the floating head 20 such that the interferometric region 45 is formed therebetween. The precise positioning of the optical fiber 40 is dependent on whether the optical fiber 40 has an angled polished end or not. The figure depicts a preferred embodiment wherein two optical fibers 40 are positioned with respect to the side 27 of the floating head 20 to receive a reflection therefrom and to obtain measurements in two directions.

Figure 10A:
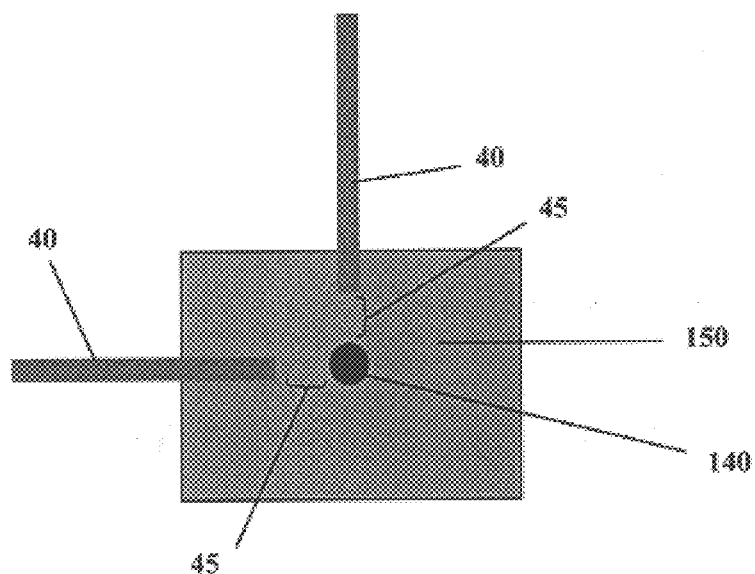
FIG. 10A is a bottom view of a physical arrangement of the fiber optic wall shear stress sensor of the present invention where the floating head is supported on an elastic base and the interferometric region is formed between a reflector and an optical fiber.
Figure 10B:
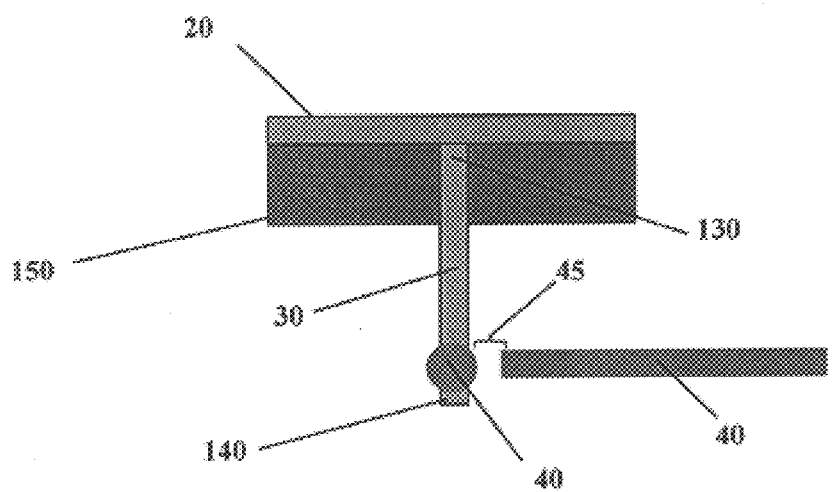
FIG. 10B is a side view of a physical arrangement of the fiber optic wall shear stress sensor of the present invention where the floating head is supported on an elastic base and the interferometric region is formed between a reflector and an optical fiber.

FIGS. 10A and 10B depict a similar arrangement to that of FIGS. 9A and 9B, where the floating head 20 is attached to an elastic base 150. A reflector 30 is positioned with respect to the floating head such that the underside of the floating head 20 is attached to a first end 130 of the reflector 30. Each optical fiber 40 is positioned with respect to a side 140 of the reflector 30 such that an interferometric region 45 is formed therebetween. When the optical fiber 40 is straight ended, it is positioned perpendicular to the reflector 30. However, if the optical fiber 40 has an angled polished end, the angled polished end is positioned in parallel to the reflector 30. Such placement of the optical fibers allows for measurement in two directions.

Figure 11:
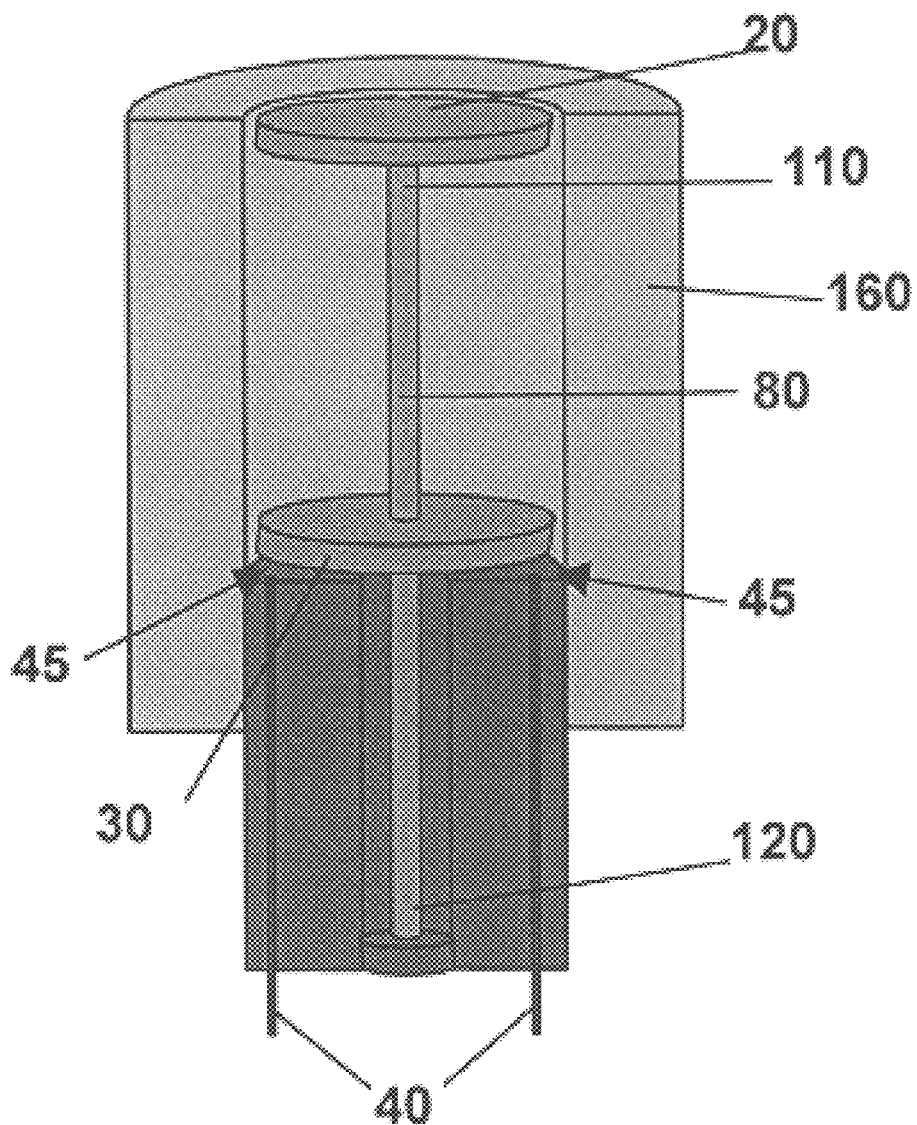
FIG. 11 is a cross-sectional view of the most preferred embodiment of the invention for a physical arrangement of the fiber optic wall shear stress sensor of the present invention.

FIG. 11 depicts the most preferred embodiment of the invention, where a floating head 20 is supported by a first end 110 of a cantilever beam 80. A reflector 30 is attached to a second end 120 of the cantilever beam 80. The reflector 30 moves in response to the floating head 20. First and second optical fibers 40 are positioned in an operable relationship to the reflector 30 wherein an interferometric region 45 is formed therebetween. The interferometric region changes in response to a shear force on the floating head 20. A housing 160 surrounds the floating head 20, cantilever beam 80, reflector 30, and the first and second optical fibers 40.

Many of the figures depict the preferred cantilever beam physical arrangement. However, any physical arrangement known to those skilled in the art may be substituted for the cantilever beam. For example, the cantilever beam may be replaced with a spring or similar means. In addition, more than one cantilever beam may be used as the physical arrangement.

When using the fiber optic sensor of the present invention to measure a wall shear stress, any one of the arrangements previously described is provided along with a light source. Light is directed through the optical fiber and the sensor is exposed to a fluid flow. Upon exposure, the floating head is deflected and a change in the interferometric region occurs. Light is reflected back through the optical fiber. The change in the interferometric region is measured and the measurement is correlated to a wall shear stress. The process may be modified by adding the step of heating the floating head to a temperature approximately equal to the wall temperature. This allows for minimization of errors resulting from temperature differences between the floating head and the wall. In addition, the floating head may be cooled to a temperature approximately equal to the wall temperature. Cooling of the floating head may be achieved by running water through a member supporting the floating head.

EXAMPLES

Example 1

Figure 12:
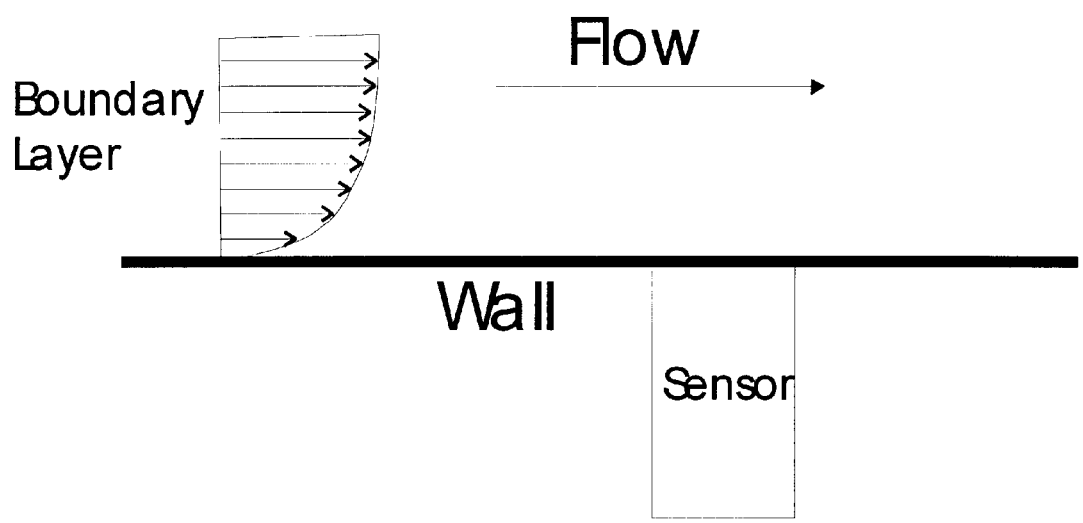
FIG. 12 is a diagram of how the wall shear stress measurement is performed using the present invention.

A wall shear stress gage having a cantilever beam as the physical arrangement, as shown in FIG. 11, was fabricated according to the following process. A cantilever beam, reflector, and floating head were lathed out of a piece of metal. The cantilever beam was fitted into a thick-walled hollow cylinder. Holes for two optical fibers were drilled lengthwise down the length of the cylinder. The optical fibers were fed through the holes and the ends of the fibers were affixed so as to be even with the top of the cylinder. The cantilever beam was slid into place so that the reflector and the optical fibers were brought into close proximity and were aligned. The cantilever beam and the cylinder were attached to each other forming an arrangement. The arrangement was placed into a housing, and in particular a larger hollow cylinder. A small gap was left surrounding the floating head at the end of the cantilever beam and the housing. The top of the housing and the free surface of the floating head were even and attached to each other. The completed gage was installed for measurement by assuring that the free surface of the floating head was even with the surface of the wall of the fluid flow where the shear stress was measured as shown in FIG. 12.

Example 2

The wall shear stress gage fabricated in Example 1 was tested in a supersonic wind tunnel. A Mach 3 nozzle was installed. Two runs were conducted in a Mach 3 flow and gap information was collected by a demodulation system. This information was converted to forces through a calibration and a coefficient of friction was calculated according to the following equation:

$$C_f = \tau_w / (\gamma/2) P_\infty M^2_\infty$$

Previous experiments with conventional strain gage designs measured $C_f=0.0015$ and predictions using the Schultz-Grunow correlation predict $C_f=0.0014$. Testing with the fiber optic gage of the present invention yielded a $C_f=0.00125$ for the first test and $C_f=0.00121$ for the second test. The output of the sensor for the complete test showed important characteristics: a near constant value during the steady portion of the tun and the return to zero at the end of the run. Both of these characteristics have been difficult to achieve with conventional strain gage designs.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A fiber optic wall shear stress sensor comprising:
   a floating head supported by a physical arrangement; and
   at least one optical fiber positioned in an operable relationship to the floating head wherein an interferometric region is formed between the floating head and each optical fiber and wherein the interferometric region changes in response to a shear force on the floating head.

2. A fiber optic wall shear stress sensor according to claim 1, wherein the floating head is moveable and non-nulling.

3. A fiber optic wall shear stress sensor according to claim 1, wherein the floating head is nulling.

4. A fiber optic wall shear stress sensor according to claim 1, wherein the physical arrangement is selected from the group consisting of: a cantilever beam, a spring, a flexure, and an elastic support.

5. A fiber optic wall shear stress sensor according to claim 4, wherein the physical arrangement is a cantilever beam.

6. A fiber optic wall shear stress sensor according to claim 1, wherein the floating head is supported by a plurality of tethers attached to a support structure and wherein the interferometric region is formed between each optical fiber and a surface of the floating head.

7. A fiber optic wall shear stress sensor according to claim 6, wherein each optical fiber has an angled polished end, wherein the interferometric region is formed between each angled polished end and a surface of the floating head.

8. A fiber optic wall shear stress sensor according to claim 1, wherein the physical arrangement is at least one cantilever beam having a first end and a second end, wherein the floating head has a side serving as a reflector and an underside and wherein the floating head is supported on a portion of the underside by the first end of each cantilever beam, and wherein the interferometric region is formed between each optical fiber and the side of the floating head serving as the reflector.

9. A fiber optic wall shear stress sensor according to claim 8, wherein each optical fiber has an angled polished end and wherein the interferometric region is formed between the angled polished end and the side of the floating head serving as the reflector.

10. A fiber optic wall shear stress sensor according to claim 1, wherein the physical arrangement is at least one cantilever beam having a first end and a second end, wherein the floating head has an underside serving as a reflector and is supported on a portion of the underside by the first end of each cantilever beam, and wherein the interferometric region is formed between each optical fiber and the underside of the floating head serving as the reflector.

11. A fiber optic wall shear stress sensor according to claim 10, wherein each optical fiber has an angled polished end and wherein the interferometric region is formed between each angled polished end and the underside of the floating head serving as the reflector.

12. A fiber optic wall shear stress sensor according to claim 1, wherein the physical arrangement is an elastic base attached to a portion of an underside of the floating head and wherein a side of the floating head serves as a reflector, and wherein the interferometric region is formed between each optical fiber and the side of the floating head.

13. A fiber optic wall shear stress sensor according to claim 12, wherein each optical fiber has an angled polished end and wherein the interferometric region is formed between each angled polished end and the side of the floating head.

14. A fiber optic wall shear stress sensor comprising:
a floating head supported by a physical arrangement;
a reflector positioned in an operable relationship to the floating head, wherein the reflector moves in response to the floating head; and
at least one optical fiber positioned in an operable relationship to the reflector, wherein an interferometric region is formed between each optical fiber and the reflector and wherein the interferometric region changes in response to a shear force on the floating head.

15. A fiber optic wall shear stress sensor according to claim 14, wherein the floating head is moveable and non-nulling.

16. A fiber optic wall shear stress sensor according to claim 14, wherein the floating head is nulling.

17. A fiber optic wall shear stress sensor according to claim 14, wherein the physical arrangement is selected from the group consisting of: a cantilever beam; a spring; a flexure; and an elastic support.

18. A fiber optic wall shear stress sensor according to claim 17, wherein the physical arrangement is a cantilever beam.

19. A fiber optic wall shear stress sensor according to claim 14, wherein the floating head is supported by a plurality of tethers attached to a support structure; wherein the reflector has a first end and a side, wherein a portion of an underside of the floating head is attached to the first end of the reflector and wherein the interferometric region is formed between each optical fiber and the side of the reflector.

20. A fiber optic wall shear stress sensor according to claim 19, wherein each optical fiber has an angled polished end, wherein the interferometric region is formed between each angled polished end and the side of the reflector.

21. A fiber optic wall shear stress sensor according to claim 14, wherein the physical arrangement is at least one cantilever beam having a first side and a second side, wherein the floating head is supported on the first side of each cantilever beam, and wherein the interferometric region is formed between each optical fiber and the second side of each cantilever beam which serves as the reflector.

22. A fiber optic wall shear stress sensor according to claim 21, wherein each optical fiber has an angled polished end wherein the interferometric region is formed between each angled polished end and the second side of the cantilever beam which serves as the reflector.

23. A fiber optic wall shear stress sensor according to claim 14, wherein the physical arrangement is a pair of cantilever beams wherein each cantilever beam has a first side and a second side, wherein one of the cantilever beams serves as the reflector and, wherein the floating head is supported on the first side of each cantilever beam; and wherein the interferometric region is formed between each optical fiber and the second side of the cantilever beam serving as the reflector.

24. A fiber optic wall shear stress sensor according to claim 23, wherein each optical fiber has an angled polished end and wherein the interferometric region is formed between each angled polished end and the second side of the cantilever beam serving as the reflector.

25. A fiber optic wall shear stress sensor according to claim 14, wherein the floating head is attached to an upperside of a reflector and wherein the reflector is larger than the floating head; a cantilever beam attached to a portion of an underside of the reflector; and wherein the interferometric region is formed between each optical fiber and the underside of the reflector.

26. A fiber optic wall shear stress sensor according to claim 25, wherein each optical fiber has an angled polished end and wherein the interferometric region is formed between each angled polished end and the underside of the reflector.

27. A fiber optic wall shear stress sensor according to claim 14, wherein the physical arrangement is an elastic base attached to a portion of an underside of the floating head; wherein the reflector has a first end and a side, wherein a portion of the underside of the floating head is attached to the first end of the reflector and wherein the interferometric region is formed between each optical fiber and the side of the reflector.

28. A fiber optic wall shear stress sensor according to claim 27, wherein each optical fiber has an angled polished end and wherein the interferometric region is formed between each angled polished end and the side of the reflector.

29. A fiber optic wall shear stress sensor comprising:
a floating head supported by a first end of a cantilever beam;
a reflector attached to a second end of the cantilever beam wherein the reflector moves in response to the floating head;
first and second optical fibers positioned in an operable relationship to the reflector wherein an interferometric region is formed between the first and second optical fibers and the reflector wherein the interferometric region changes in response to a shear force on the floating head; and
a housing surrounding the floating head; cantilever beam; reflector; and the first and second optical fibers.

30. A process for measuring wall shear stress with a fiber optic sensor, the process comprising the steps of:

providing a fiber optic wall shear stress sensor comprising a floating head supported by a physical arrangement; and at least one optical fiber positioned in an operable relationship to the floating head wherein an interferometric region is formed between the floating head and each optical fiber and wherein the interferometric region changes in response to a shear force on the floating head; directing light through the optical fiber;

exposing the fiber optic wall shear stress sensor to a fluid flow wherein the floating head is deflected causing a change in the interferometric region and light is reflected back through the optical fiber; and measuring the change in the interferometric region and correlating the measurement to a wall shear stress.

31. A process according to claim 30, further comprising the step of heating the floating head to a temperature approximately equal to the wall temperature.

32. A process according to claim 30, further comprising the step of cooling the floating head to a temperature approximately equal to the wall temperature.

33. A process according to claim 32, wherein the floating head is cooled by running water through a member supporting the floating head.

34. A process for measuring wall shear stress with a fiber optic sensor, the process comprising the steps of:

providing a fiber optic wall shear stress sensor comprising a floating head supported by a physical arrangement; a reflector positioned in an operable relationship to the floating head, wherein the reflector moves in response to the floating head; and at least one optical fiber positioned in an operable relationship to the reflector, wherein an interferometric region is formed between each optical fiber and the reflector and wherein the interferometric region changes in response to a shear force on the floating head;

directing light through the optical fiber;

exposing the fiber optic wall shear stress sensor to a fluid flow wherein the floating head is deflected wherein a change in the interferometric region occurs and wherein the light is reflected from the reflector back through the optical fiber; and measuring the change in the interferometric region and correlating the measurement to a wall shear stress.

35. A process according to claim 34, further comprising the step of heating the floating head to a temperature approximately equal to the wall temperature.

36. A process according to claim 34, further comprising the step of cooling the floating head to a temperature approximately equal to the wall temperature.

37. A process according to claim 36, wherein the floating head is cooled by running water through a member supporting the floating head.

* * * * *

UNITED STATES PATENT AND TRADEMARK OFFICE
CERTIFICATE OF CORRECTION

PATENT NO. : 6,426,796 B1  
DATED : July 30, 2002  
INVENTOR(S) : Wade J. Pulliam, Joseph A. Schetz, Mark E. Jones, Kent A. Murphy and Scott A. Meller It is certified that error appears in the above-identified patent and that said Letters Patent is hereby corrected as shown below:

<u>Title page,</u>  
Item [75], the Inventors are:  
-- Wade J. Pulliam  
Joseph A. Schetz  
Mark E. Jones  
Kent A. Murphy  
Scott A. Meller --

Signed and Sealed this

Twenty-sixth Day of November, 2002

Attest:

JAMES E. ROGAN  
Director of the United States Patent and Trademark Office

Attesting Officer